(12) United States Patent
Lawson et al.

(10) Patent No.: US 7,639,145 B2
(45) Date of Patent: Dec. 29, 2009

(54) METHOD AND APPARATUS FOR COMMUNICATING AN ALARM WHILE MONITORING

(75) Inventors: Corey James Lawson, Sussex, WI (US); George Martin Hutchinson, Milwaukee, WI (US); Elizabeth Anne Bock, Elm Grove, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 1380 days.

(21) Appl. No.: 10/834,625

(22) Filed: Apr. 29, 2004

(65) Prior Publication Data

US 2004/0249249 A1 Dec. 9, 2004

Related U.S. Application Data

(63) Continuation-in-part of application No. 10/440,626, filed on May 19, 2003, now Pat. No. 7,079,035.

(51) Int. Cl.
*G08B 23/00* (2006.01)
*A61B 5/00* (2006.01)

(52) U.S. Cl. .................................. 340/573.1; 600/301

(58) Field of Classification Search ................. 340/500, 340/501, 573.1, 539.12, 7.55, 7.56, 309.16, 340/3.1, 3.9; 600/300, 301, 306, 323, 324, 600/346–348
See application file for complete search history.

(56) References Cited

U.S. PATENT DOCUMENTS

| | | | |
|---|---|---|---|
| 5,262,944 A * | 11/1993 | Weisner et al. .............. | 600/300 |
| 5,464,012 A | 11/1995 | Falcone | |
| 5,469,144 A | 11/1995 | Gradzki et al. | |
| 5,865,736 A | 2/1999 | Baker, Jr. et al. | |
| 6,057,758 A | 5/2000 | Dempsey et al. | |
| 6,248,067 B1 | 6/2001 | Causey et al. | |
| 6,315,719 B1 | 11/2001 | Rode et al. | |
| 6,569,095 B2 | 5/2003 | Eggers | |
| 6,658,276 B2 * | 12/2003 | Kianl et al. ................. | 600/322 |
| 6,754,516 B2 | 6/2004 | Mannheimer | |
| 6,822,564 B2 * | 11/2004 | Al-Ali ........................ | 340/511 |
| 7,081,095 B2 * | 7/2006 | Lynn et al. .................. | 600/538 |
| 7,247,154 B2 * | 7/2007 | Hickle ........................ | 604/500 |
| 7,403,834 B2 * | 7/2008 | Poolla et al. ................ | 700/121 |
| 7,468,032 B2 * | 12/2008 | Stahmann et al. ........... | 600/301 |

OTHER PUBLICATIONS

Dr. R. Fried, et al. (2001) "Online Pattern Recognition in Intensive Care Medicine" 2001 AMIA Annual Symposium, Nov. 3-7, 2001, Washington D.C.

(Continued)

*Primary Examiner*—Jennifer Mehmood
(74) *Attorney, Agent, or Firm*—Andrus, Sceales, Starke & Sawall, LLP

(57) ABSTRACT

Method and apparatus for displaying an alarm condition on a patient monitor. A graphical user interface can include an alarm communication device that indicates a state of a physiological parameter. The alarm communication device can include a stable region, an intermediate region, and a critical region. At least one of the intermediate region and the critical region can represent the alarm condition. The graphical user interface can also include a tolerance control that adjusts at least one of a boundary and a width of at least one of the stable region, the intermediate region, and the critical region in order to adjust the alarm condition.

56 Claims, 10 Drawing Sheets

OTHER PUBLICATIONS

R. Schoenberg, M.D. et al., (1999) "Making ICU Alarms Meaningful: a comparison of traditional v. trend-based algorithms," AMIA Annual Symposium, Nov. 6-10, 1999.

A. Lowe, et al. (1999) Diagnostic Monitoring in Anesthesia Using Fuzzy Trend Templates for Matching Temporal Patterns, Artificial Intelligence in Medicine 16.

* cited by examiner

METHOD AND APPARATUS FOR COMMUNICATING AN ALARM WHILE MONITORING

CROSS-REFERENCE TO RELATED APPLICATIONS

This application is a continuation-in-part of U.S. patent application Ser. No. 10/440,626, filed May 19, 2003 now U.S. Pat. No. 7,079,035, the subject matter of which is incorporated herein by reference.

BACKGROUND OF THE INVENTION

Monitors are used to monitor all sorts of variables to look for the occurrence of certain noteworthy events. Many actions taken by a subject can generate events that generate data that looks like an alarm, but is merely an artifact. For instance, if a patient moves around, a sensor attached to the patient may generate a data signal that would be indicative of an abnormal condition. This false positive result (registering that an event has occurred when in fact no significant event has occurred) would preferably not result in an alarm being generated.

Many subjects, such as patients, differ from each other in many respects that are material to monitoring. For instance, a typical person may have a normal systolic blood pressure of 120, whereas an individual's normal systolic blood pressure may be closer to 100. Some values of a systolic blood pressure may be reasonable for the typical person where they would not be as reasonable for the individual.

Additionally, readings from a patient may go from a high point in a range that is not alarming for a subject to a low point in the range that is also not alarming. While the values themselves may not be very alarming, the change in value may be significant. For instance, a value that is steadily dropping may be indicative of a problem that is gradually worsening. Also, a value that drops quickly may be a sign that something has gone wrong, even if the value remains in a normal range for the subject.

BRIEF DESCRIPTION OF THE INVENTION

It would be desirable to have a monitor that can indicate when an event has occurred where most of the indicated events are significant. It would also be desirable to avoid registering false positives, while avoiding false negatives (not registering the occurrence of a significant event).

A monitor that could use limits based on the characteristics of the subject, including typical values for the subject, would be preferable. A monitor that could use limits based on the historical characteristics of a subject would be desirable.

A system that can indicate when the readings are fluctuating, when such fluctuation is important, would be preferable. A system that can identify a relevant event indicated by the fact that the readings are changing over longer periods of time would be desirable.

A system that communicates alarms in a simple and easy-to-understand manner is desirable.

Accordingly, one or more embodiments of the invention provide a method and apparatus for displaying an alarm condition on a patient monitor. In some embodiments, a graphical user interface can include an alarm communication device that indicates a state of a physiological parameter. The alarm communication device can include a stable region, an intermediate region, and a critical region. At least one of the intermediate region and the critical region can represent the alarm condition. The graphical user interface can also include a tolerance control that adjusts at least one of a boundary and a width of at least one of the stable region, the intermediate region, and the critical region in order to adjust the alarm condition.

Other features and advantages of the invention will become apparent to those skilled in the art upon review of the following detailed description, claims and drawings.

DETAILED DESCRIPTION OF THE INVENTION

Figure 1:
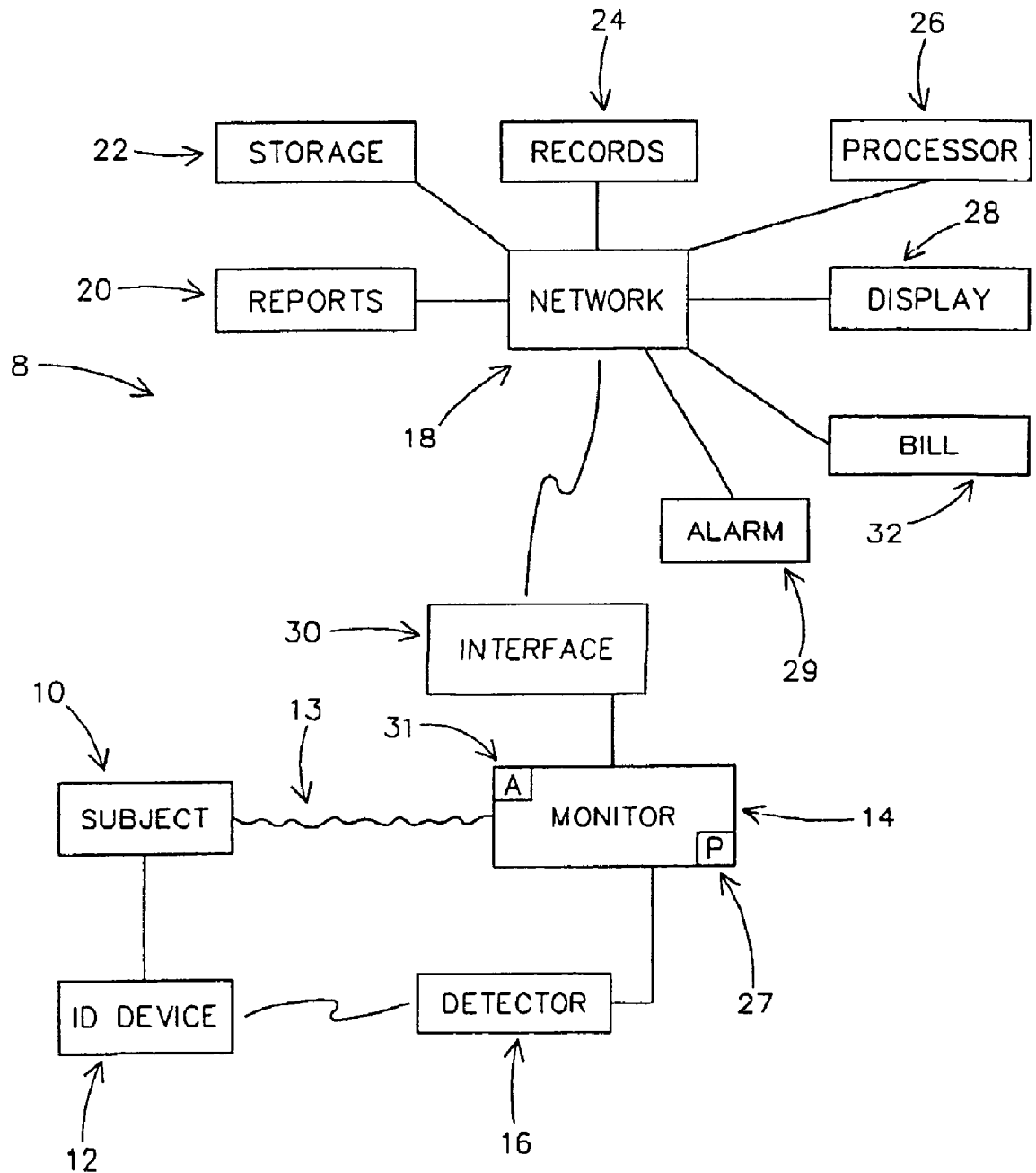
FIG. 1 illustrates a monitoring system according to one embodiment of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and can include electrical connections or couplings, whether direct or indirect.

In addition, it should be understood that embodiments of the invention include both hardware and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

Referring first to FIG. 1, a monitoring system 8 comprises a monitor 14 and a network 18. Monitor 14 also comprises a network interface 30 that allows transfer of data to and from network 18. Network interface 30 is preferably configured to allow wireless transfer of data. More preferably, network interface 30 is configured to transmit data using a radio frequency. Network interface 30 may directly facilitate transfer of data across a network for the monitor, or may facilitate transfer of data by coupling the monitor to some other device that can directly facilitate transfer.

The data transferred from monitor 14 to network 18 can be raw data or can include data that has been processed. Also, data can be transferred to monitor 14 to aid, configure, and/or operate a function of monitor 14, or can serve some other purpose relating to monitor 14. For instance, the data may include a subject's history or can include previous values used when monitoring the particular subject.

Network 18 can be any type of network across which data can be transferred. For example, network 18 can be a local area network, a wide area network, and/or the Internet. Network 18 is coupled to a report generator 20, a data storage device 22, a record keeping device 24, a processor 26, and a display 28. Report generator 20 can generate a report based on, data storage device 22 can store, record keeping device 24 can make or add to a record based on, processor 26 can process, and display 28 can display data acquired by a data acquisition device 13 of monitor 14.

Monitor 14 also includes processor 27. Processor 27 may be any signal processing circuitry, such as one or more microprocessors in combination with program logic stored in memory. Processor 27 may be made of a series of sub-processors where each sub-processor performs one of the functions of processor 27. Further, processor 26 may perform the functions of processor 27. Further still, processor 27 and processor 26 may be sub-processors of another processor that is responsible for the various functions.

Figure 2:
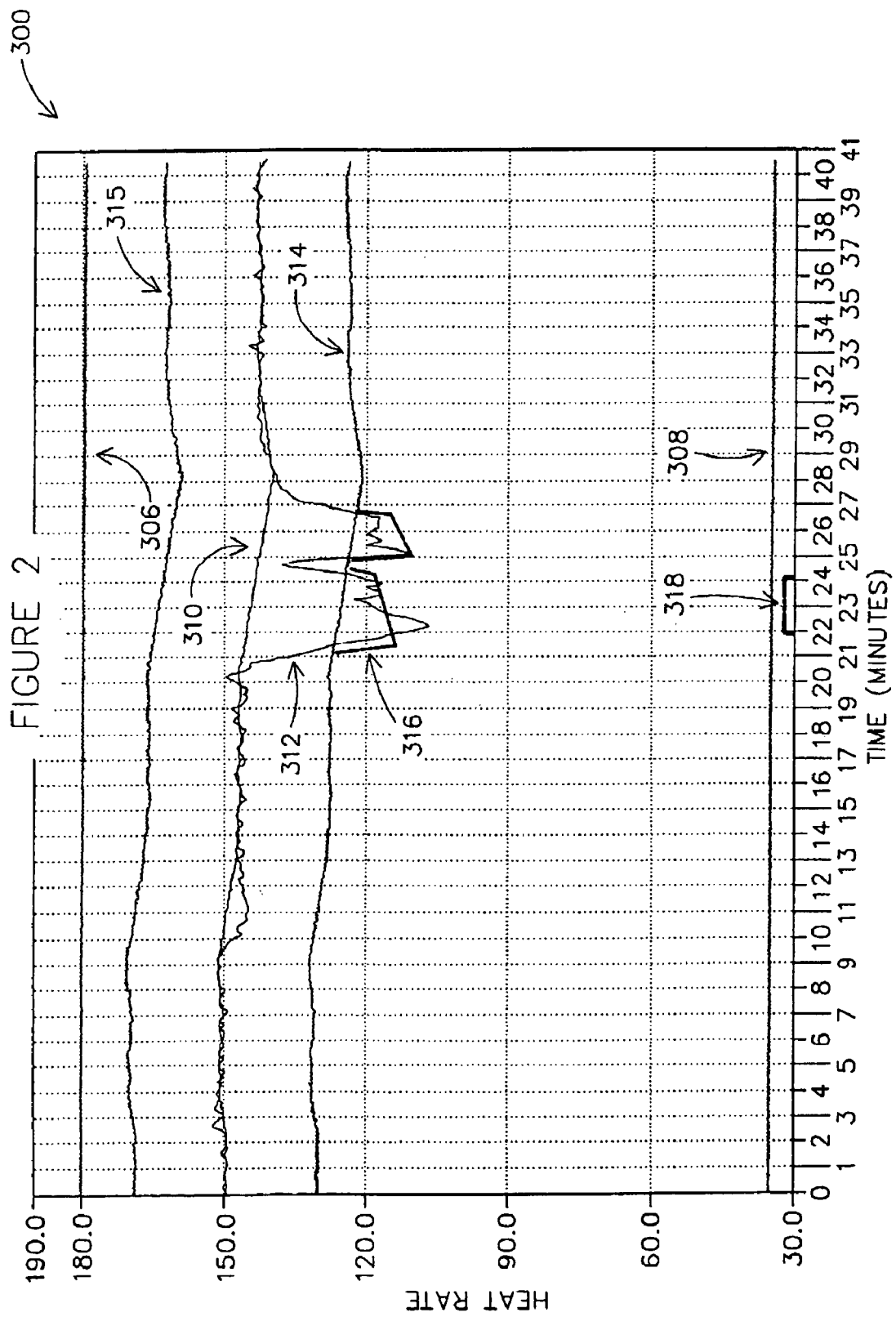
FIG. 2 is a graph illustrating alarm limits as alarm criteria where the limits are dynamically adjusted according to one embodiment of the invention.

Referring next to FIG. 2, a plot of data obtained from a monitor according to one embodiment can be seen in graph 300. Graph 300 shows a plot of heart rate (y-axis) over time (x-axis) according to one embodiment of the invention. Graph 300 shows an upper extremity limit 306, a lower extremity limit 308, a calculated representative value 310, and acquired data stream 312. Graph 300 further includes tracking thresholds 314 and 315, alarm limit 316, and alarm indicator 318.

Monitor 14 generates an alarm if the instantaneous heart rate falls outside extremity limit 306 or 308. Extremity limits 306 and 308 represent values that are extreme for the characteristic being monitored. For instance, if a patient is being monitored, the value may represent a value for the characteristic that is unlikely to be acquired from a patient who does not require immediate attention, or a value for the characteristic that represents that the patient is having (or soon will have) complications.

Monitor 14 also generates an alarm if the heart rate deviates in a predetermined manner from a calculated representative value 310. To this end, calculated representative value 310 is increased incrementally if acquired data stream 312 is greater than calculated representative value 310 at a point in time. This can be seen between the twenty-ninth minute and the thirty-second minute. Calculated representative value 310 is decreased incrementally (decremented) if acquired data stream 312 is less than calculated representative value 310 at a point in time. This can be seen between the twenty-first minute and the twenty-eighth minute.

Tracking threshold 314 is set based on calculated representative value 310. Tracking threshold 314 can be set based on a percentage difference from calculated representative value 310, based on a set amount away from calculated representative value 310, and/or based on the standard deviation of the trend (for example, as the standard deviation of calculated representative value 310 increases, the gap between calculated representative value 310 and tracking threshold 314 is increased). Tracking threshold 314 can also be set based on a combination of the previously mentioned factors, and/or any number of other factors.

Alarm limit 316 is set when acquired data 312 crosses tracking threshold 314. Alarm limit 316 can likewise be set based on any number of factors. Alarm limit 316 can be based on calculated representative value 310, tracking threshold 314, and/or any other value (of course basing alarm limit 316 on tracking threshold 314 also means that alarm limit 316 is based on calculated representative value 310 if tracking threshold 314 is based on calculated representative value 310). Alarm limit 316 is pre-configured to decrease over time as can be seen between minutes 21.5 and 24.5.

Once alarm limit 316 is set, if acquired data 312 crosses alarm limit 316 an alarm is generated as represented by bar 318. Examples of acquired data exceeding alarm limit 316 can be seen between minutes 22 and 22.8, again at about minute 23.3, and again at about minute 24. The alarm persists until alarm limit 316 is removed. The alarm can also be configured to persist based on various other criteria. For instance, the alarm may persist until acquired data no longer exceeds tracking threshold 314 or some other threshold, the alarm may be configured with a hysteresis to persist for a certain duration after acquired data 312 crosses alarm limit 316, and/or the alarm may be configured to persist until a user resets or acknowledges the alarm (i.e., it can be latching). The duration of the alarm may alternatively be based on many other factors.

Figure 3:
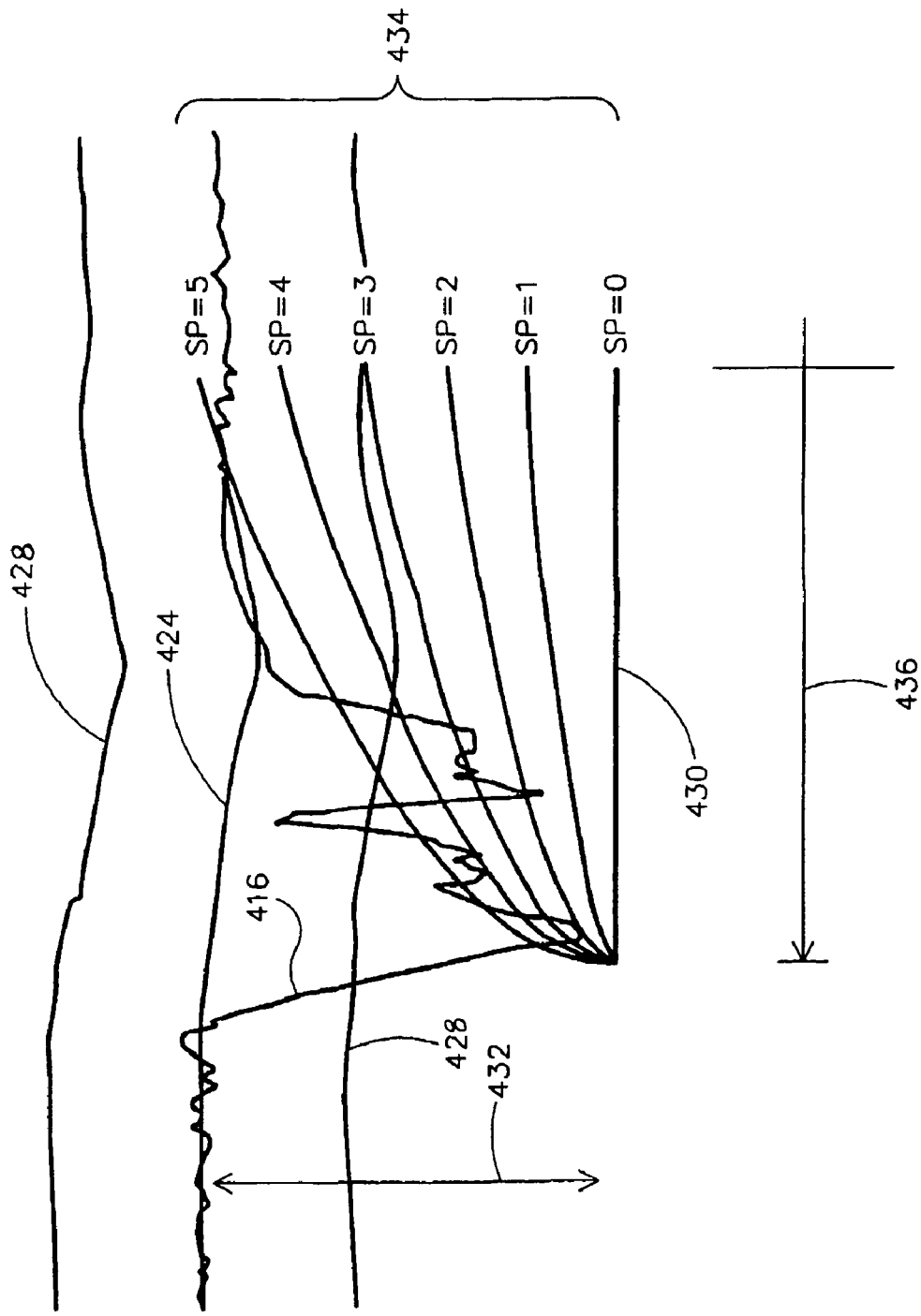
FIG. 3 is an illustration of an alarm limit that is set and that tightens when acquired data crosses a tracking threshold according to one embodiment of the invention.

In some embodiments, the value for alarm limit 316 at a point in time can be defined by the equation $AlarmCurve(t) = K + sp\sqrt{t}$, where "K" is the value of alarm limit 316 when alarm limit 316 is set and "sp" is the rate at which the curve declines (a rate of decay 434, as shown in FIG. 3). The value of "K" can be based on calculated representative value 310, acquired data 312, or some other value. The values used to calculate "K" and "sp" can be different at different points in time, and can be different for a lower alarm limit and an upper alarm limit.

Referring to FIG. 3, alarm curve 430 is calculated based on an excursion value 432 representing the maximum excursion from calculated representative value 424. Excursion value 432 can therefore be set such that if acquired data stream 416 exceeds calculated representative value 424 by more than excursion value 432, alarm curve 430 will be crossed. Alarm curve 430, however, can further include a decay rate 434, or speed of curve. Decay rate 434 represents the rate at which alarm curve 430 approaches calculated representative value 424 from excursion value 432. Alarm curve 430 may be represented by the equation: $AlarmCurve(t) = K \pm sp\sqrt{t}$ where "K" is calculated representative value 424±excursion value 432, "sp" is rate of decay 434, and "t" is time. Although a single alarm curve 430 has been described, a variety of curves and alarm thresholds 428 can be used. Alarm threshold parameters such as the illustrated excursion threshold 432, decay rate 434, and reset time 436 may be adjusted by a user to adjust alarm thresholds 428.

Figure 4:
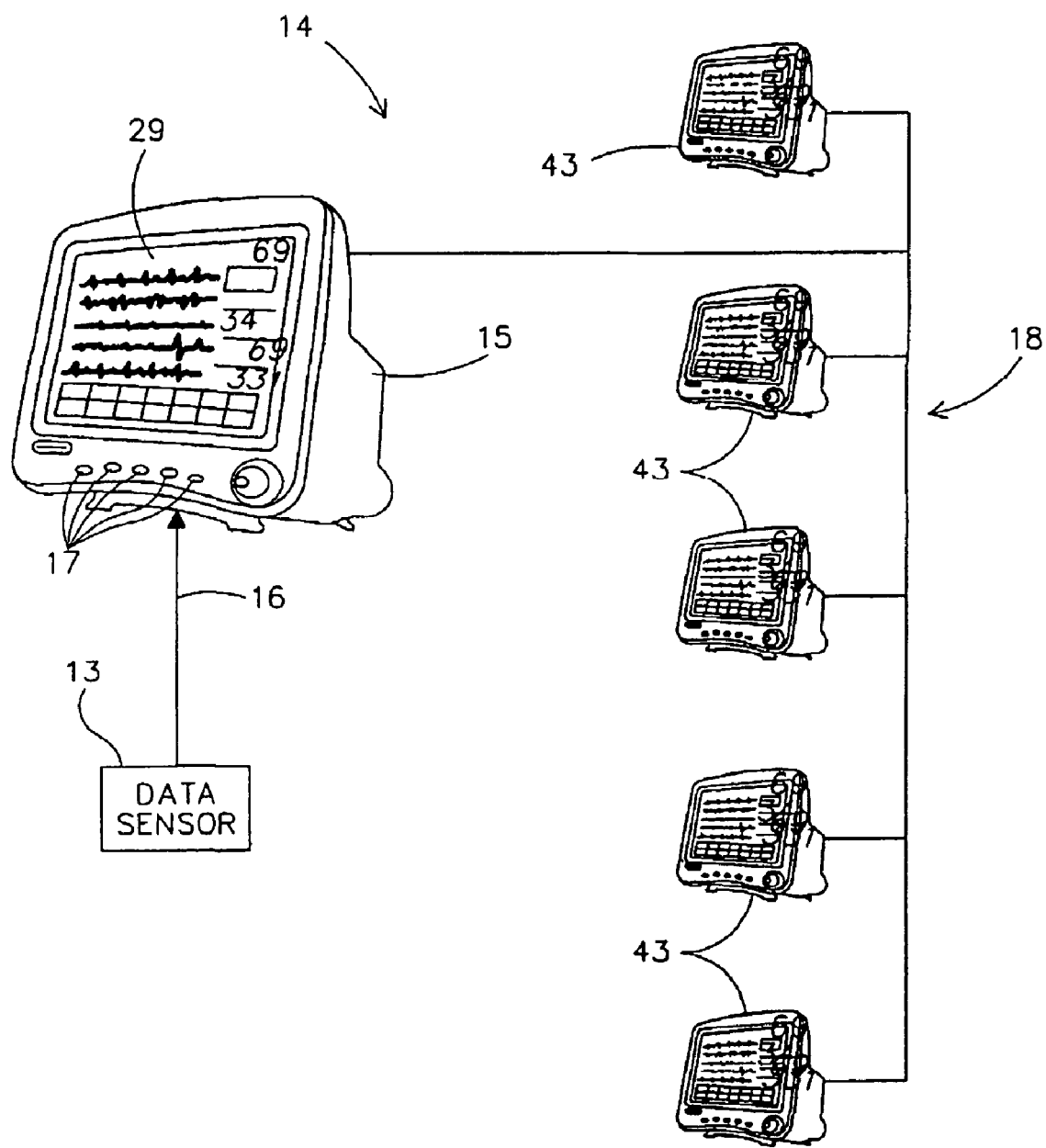
FIG. 4 illustrates a monitoring system according to another embodiment of the invention where a plurality of monitors are networked together.

Referring now to FIG. 4, a monitor 14 includes a controller 15 in communication with a data acquisition sensor 13 in order to receive a real-time data stream. The controller 15 may be utilized in combination with a variety of interactive elements such as a display 29 and control features 17 as would be comprehended by one skilled in the art. In one embodiment, the data acquired by data acquisition sensor 13 is physiological data from a patient. These characteristics include, but are not limited to, heart rate, arterial blood pressure, SpO2, CO2, EtC2, respiratory rate, and a variety of other patient physiologic responses. Also, a host of amplifiers, filters, and digitization elements may be utilized in combination with data acquisition sensor 13 as would be understood by one skilled in the art.

The extremity limits 306 and 308, tracking thresholds 314 and 315, calculated representative value 310, and incoming acquired data stream 312 can all be displayed on the display 29 such that a user can quickly and easily assess the status and settings of a subject 10. In addition, it is contemplated that the rate at which the calculated representative value is adjusted, the tracking threshold parameters, and the alarm parameters may also be displayed. Alteration of these parameters utilizing the control features 17 allows a user to fine tune the present system for a particular subject. By displaying changes in the settings, a user can be provided with a more adjustable system for generating alarms. Control features 17 could comprise a single knob that sets a single tolerance factor. The tolerance factor could then be used to adjust the various values used while monitoring. The single knob may have settings that represent tolerances from loose (alarms would generally appear less commonly) to tight (any deviation may be important).

Monitor 14 could also be networked to monitor assemblies 43 such that a subject can be moved from a single monitor 14 to any of the networked assemblies 43 while retaining information regarding calculated representative value 310, the tracking and alarm threshold calculations/parameters, and the update speed. This could allow users the ability to move a subject throughout the network while retaining all the vital monitoring information specifically set to the subject. Additionally, this could prevent monitoring from needing to start over from scratch after a move. It is contemplated that the subject can be identified after a move to a new monitor in a variety of fashions. Users may enter a subject ID number into a networked monitor 43. Alternatively, the subject may be selected from a list or database retained on the network. In other embodiments, the information may be saved onto a portable memory device for transfer to the new monitor.

Figure 5:
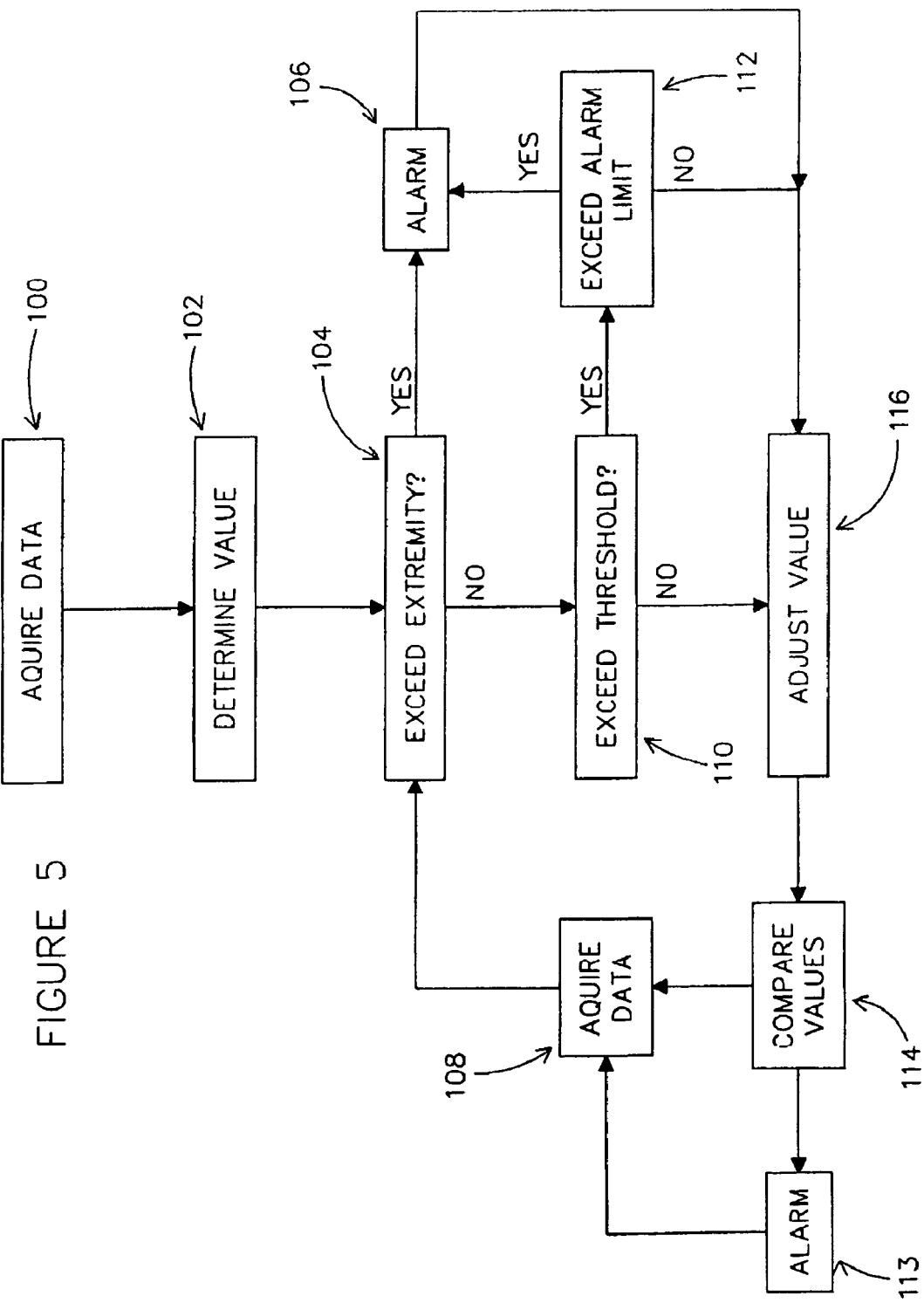
FIG. 5 is a flow chart of a method according to one embodiment of the invention.

Referring now to FIG. 5, data is acquired from a subject at block 100. The data could additionally be acquired from a database on a storage device 22, which storage device 22 could be connected to a monitor 14 over a network 18. Once data is acquired, a representative value is calculated at block 102. The value can be based on data acquired from a subject, can be data manually inputted, can be based on a tolerance factor, etc. The value can be equal to a data value or it can be some function of the data value. For instance, when monitoring blood oxygenation levels, the value can be equal to the current or typical level of oxygen in the monitored patient's blood, can be a function of both the current or typical level of oxygen in the monitored patient's blood and a standard blood oxygenation level for a typical person, can be based on a function that considers historical levels of blood oxygenation of a particular patient, etc. The representative value calculated at block 102 typically represents a normal value (or some function of a normal value) for the subject for the characteristic being monitored. For a patient, the representative value calculated at block 102 may also take into consideration the medications being taken and/or the treatments being administered.

Once the representative value is calculated at block 102, a determination is made based on whether the value crosses an extremity limit 104. If it does, an alarm is sent at block 106. The extremity limit represents a value that is extreme for the characteristic being monitored. The limit may be extreme in general, or may be extreme given the subject's characteristics and other values. An extremity limit is most useful if the tracking threshold or the alarm limit are ever allowed to cross the extremity limit. The extremity limit could alternatively be incorporated into a function used to determine a value of a tracking threshold or an alarm limit (i.e. the maximum/minimum the value of the alarm limit can be is the extremity limit value).

If the data does not cross the extremity limit at block 104, a determination is made at block 110 as to whether the data crosses a tracking threshold (such as 314 and 315) at block 110. The tracking threshold can be a preset amount different than the calculated representative value, can be some function of the calculated representative value, or can be based on some other typical value of the subject. An example of a function of the calculated representative value may include setting the tracking threshold based on how different the calculated representative value is from a typical value for an average subject, i.e., if the subject is a person, if a typical heart rate range is set between 60 and 80 beats per minute and the determined value for heart rate is 100 beats per minute, the exemplary function may set the high limit at 150 beats per minute whereas if the determined heart rate is 54 beats per minute, the exemplary function may set the high limit at 130 beats per minute. The tracking threshold may also be set based on the variability of the acquired data (i.e. if the standard deviation of the acquired data is large, then the tracking threshold is set farther from the calculated representative value 310, and if the standard deviation is small, then the tracking threshold is set closer to the calculated representative value 310).

If the data does cross the tracking threshold at block 110, a determination is made at block 112 as to whether the data meets an alarm criteria at block 112. The alarm criteria of block 112 is preferably affected by the fact that the data crossed the tracking threshold at block 110. Ways that the determination of block 110 may affect the alarm criteria of block 112 include setting the alarm criteria based on the determination of block 110, and/or tightening the alarm criteria of block 112 based on the determination at block 112. For example, the alarm criteria at block 112 may continually exist, but will tighten if the data crosses the threshold at block 110.

If the alarm criteria of block 112 is set to tighten if the tracking threshold is crossed, the duration of tightening can be preset, can be based on a tolerance factor, can be based on the results of other monitors, can be based on whether prior acquired data did and/or how close prior acquired data was to meeting the alarm criteria, can be based on a subject's history, can be based on the trend of the acquired values, can be based on whether the data continues to exceed the tracking threshold, and/or can be based on some other factor.

Sending an alarm at block 106 could involve a variety of factors. Also, some users may desire to include additional steps when sending an alarm at block 106. Some additional steps may include checking for the signaling of other alarms based on other criteria, other settings relating to the monitor or the monitored subject, customized settings for a particular facility/user, etc.

If an alarm is sent at block 106, the data does not meet the alarm criteria at block 112, or the data does not cross the tracking threshold at block 110, the calculated representative value is adjusted at block 116. The adjustment can be made every time, every set period of time, a time period based on the difference between the data and the calculated representative value, etc. The rate of adjustment can also be based on the amount of data acquired since the last adjustment, and/or the amount of agreement of the data (such as standard deviation) since the last adjustment. Also, when an acquired data value results in an alarm at block 106 (or meets some other criteria), block 116 may be skipped. Skipping block 116 may be one way of avoiding the incorporation of data that is not representative of a typical value for the subject for the characteristic being monitored.

Adjustment to the tracking threshold and/or the calculated representative value can be made in any number of ways based on the acquired data. For instance, if the newly acquired data point is greater than the calculated representative value, then the calculated representative value may be increased by a preset amount. This process could also be the reverse if the newly acquired data point is less than the calculated representative value.

Also, various data can be used to adjust the value at block 116. For instance, every value may be used unless the value results in an alarm at block 106, crosses the threshold at block 110, or meets some other criteria for non-inclusion. Also, the most recent data may be more heavily weighted, older data may be ignored, and/or some other criteria may be used.

Instead of adjusting the calculated representative value at block 106, the value of the tracking thresholds and/or alarm criteria can be adjusted directly. For instance, a tracking threshold may be reset based on whether the average value of the newly acquired data is greater than or less than a median point between two tracking thresholds (or than a point a certain distance from the threshold)—raising the threshold if greater, and lowering the threshold if less. The criteria for adjusting these values can also include factors such as those mentioned previously for adjusting the typical value.

Once the typical value is adjusted at block 116, values can be compared at block 114. Comparison at block 114 can include a determination whether a comparison of recorded values should be made. The determination may be based on time, on number of recorded values, or on some other criteria. If the determination is made based on time, the amount of time between values in the comparison is preferably greater than about 10 minutes, and more preferably, the values are separated by at least about 30 minutes. The amount of time between values is also preferably no more than about twenty-four hours, and more preferably no more than about 4 hours.

If based on amount of data received, the limits for amount of data would preferably be chosen such that they would generally meet similar time frames.

If a comparison is to be made at block 114, the comparison may be based upon two or more values, or two or more sets of values. Further, the comparison may include determining the difference in values, the comparison could include a trend analysis, and/or the comparison could include any number of other criteria. The comparison can be based on a plurality of the past values equally, a time weighted comparison of the values, a trend analysis of the values, a comparison of a small number of values, etc.

The comparison at block 114 could also include determining the change in a patient's values over time (i.e. determine the slope of the values). If slopes are determined, a plurality of values can be used to generate a plurality of slopes. For instance, each slope can represent an average change over a two or three minute time period. The values of a plurality of slopes can be compared. This comparison can include calculating a mean value and a standard deviation of the slopes over a set period, such as two or three hours or two or three days. A comparison of the slopes may be used to give an idea of the condition of a patient (for instance a patient who is steadily getting worse). For instance, a patient with a mean slope that shows decreasing values with respect to time and a low standard of deviation may be gradually worsening. This may be judged by comparing the mean slope and/or standard deviation to preset thresholds.

An alarm can be then sent at block 113 based on the comparison of block 114. The alarm can be based on whether the results of the comparison exceed a preset limit, based on a tolerance factor, based on other characteristics of the subject, and/or based on some other criteria.

Once the values have been compared at block 114, data can be acquired at block 108, and the process can proceed back to block 104.

A tolerance factor can be used to affect the parameters that are used. For example, a tolerance factor can be used to set the typical value, a tracking threshold, an alarm criteria, the rate at which values are adjusted, the rate at which an alarm criteria tightens, etc. A tolerance factor can also be used to affect the sensitivity allowed for the comparison at block 114.

The tolerance factor can be based on a number of different things. For example, the tolerance factor can be based on a factor chosen by a user, a subject's history, a subject's reason for being monitored, other measured values of a patient, the value of the typical value calculated at block 102 or adjusted at block 116, and/or some other criteria. Additionally, the tolerance factor may be adjusted by a user, may be adjusted based on information relating to subject 10, and/or may be adjusted based on the amount of data inputted from subject 10 (the more data that has been inputted, the more likely the alarm criteria accurately represents the subject). The tolerance factor may change over time and may be different for different applications of the alarm criteria to the subject 10.

Referring again to FIG. 1, monitor 14 comprises an identity detector device 16 configured to identify a subject 10. Identity detector device 16 can identify subject 10 by detecting an identification device 12 associated with a subject of interest 10. Identification device 12 can be a card or other object associated with the subject. Identification device could be used for wireless identification of subject 10 and/or identification device 12 could be a computer readable medium.

Also, bill generator 32 can generate a bill based on the use of monitor 14. Bill generator 32 can generate a bill for the use of monitor 14, or can integrate the use of monitor 14 into a larger bill to be sent. Bill generator 32 can also monitor the usage of monitor 14, and generate reports based on usage of monitor 14. Bill generator 32 can also be used to send a notice to a person across network 18 indicating that monitor 14 is being used and billed. People that may desire receiving such a notice might include a patient's primary physician, a treating physician, an insurance carrier, and a patient. Delivering a notice to an insurance carrier may allow faster approval for sudden, unexpected usage of monitor 14. This would allow a hospital to collect funds sooner, and would allow a patient to worry less about obtaining coverage after treatment has been completed. Once the bill is generated, it can then be sent physically or electronically to a recipient. The recipient may be a computer at an insurance company that calculates the extent of coverage and the amount to be paid based on the usage of monitor 14.

Further, an alarm signal sent by processor 27 may be sent to an alarm signaling device 31 physically connected to processor 27, or may be sent to an alarm signaling device 29 located remote from processor 26. Remote alarm signaling device 29 may be a part of a pager or some other type of communication device. Remote alarm signaling device 29 could also be located at a discrete location such as at a nurse's station in a health care facility.

Alarms generated by alarm signaling devices 29 and 31 may take on any form including, but not limited to, an audible sound, a visual indicator, a message, and a vibrating alert. The alarm generated by alarm signaling devices 29 and 31 can further include a message indicating the reason for the alarm. The alarm could also be differentiated based on a number of criteria including the type and severity of the event causing the alarm. If a system has more than one type of alarm that can be generated, the alarms can each be used to alert different healthcare personnel, depending on the severity and type of alarm. Further, if a system has more than one alarm signaling device, the device that signals the alarm could be differentiated based on a number of criteria including the type and severity of the event underlying the alarm.

Reference to "tightening" of alarm criteria means that more situations will be covered by the alarm criteria. For instance, when the alarm criteria includes an alarm limit whose value is set based on the value of a typical value for a subject, tightening the alarm criteria could include reducing the difference between the alarm limit and the typical value.

Reference to "dynamically tightening" the alarm criteria refers to a situation, as in FIG. 3, where the alarm criteria continues to tighten over a set period of time.

FIGS. 6-10 illustrate a patient monitor 600 according to one embodiment of the invention. The patient monitor 600 can include a user interface 601. The user interface 601 can include a primary display portion 602 for displaying physiological data as it is acquired from a patient and a secondary display portion 604 for displaying details relating to the primary display portion 602. In some embodiments of the invention, as illustrated in FIGS. 6-10, the user interface 601 can include at least a portion of the primary display portion 602 and the secondary display portion 604. In other embodiments, the user interface 601 can include one of the primary display portion 602 and the secondary display portion 604, while the other is hidden from or accessible by a user. In still other embodiments, the user interface 601 can include a portion of the primary display portion 602 or a portion of the secondary display portion 604. In yet other embodiments, the user interface 601 can include a portion of the primary display portion 602 and a portion of the secondary display portion 604. As a result, the user interface 601 can be tailored to meet a user's needs, and the user interface 601 need not include all of the elements that are illustrated in FIGS. 6-10.

The primary display portion 602 can include a chart 606 that displays an acquired data stream 608 (e.g., in real-time) of acquired patient data. The primary display portion 602 can also include a current data display 610, an alarm communication device 612, a tolerance control 614 for tightening or loosening at least one tolerance factor, and a data analysis speed control 616 for controlling the speed at which data is displayed on the chart 606 for detailed analysis by clinicians.

In one embodiment, the chart 606 can display an acquired data stream 608 representative of the patient's heart rate (y-axis), shown in beats per minute (bpm), over time (x-axis), with each marking along the x-axis representing a time period (e.g., five minutes). The chart 606 can be formulated to display any acquired physiological data, as discussed above, and heart rate is shown and described by way of example only. A pointer 620 can point to a position on the chart 606 where currently-acquired data is being plotted. The data point (e.g., a numeric value) of the data stream 608 that corresponds to the position on the x-axis of the pointer 620 can be displayed in the current data display 610. Alternatively, a current calculated representative value 622 of the acquired patient data can be displayed in the current data display 610. The current data point in the data stream 608, as well as the current calculated representative value 622, can change over time as new data is acquired from the patient. Accordingly, the value in the current data display 610 can change over time.

The chart 606 can further display the calculated representative value 622. The calculated representative value 622 can be based on the acquired data stream 608 and can be used to smooth the waveform of the acquired data stream 608. As explained above, the calculated representative value 622 can increment when the acquired data stream 608 is greater than the previous calculated representative value 622 at a point in time, and the calculated representative value 622 can decrement when the acquired data stream 608 is less than the previous calculated representative value 622 at a point in time. The calculated representative value 622 can increment or decrement, depending on the acquired data stream 608. The amount by which the calculated representative value 622 is incremented or decremented can depend on the setting of a "tracking speed" knob 700, which is illustrated in the secondary portion 604 of the user interface 601. The tracking speed knob 700 can be set to a variety of discrete settings that determine a fixed amount by which the calculated representative value 622 is incremented or decremented, depending on whether the most-recently acquired patient data point falls above or below the calculated representative value 622. For example, if the previous calculated representative value 622 at a given point in time is 70 bpm, and the next acquired patient data point is 72 bpm, then the next calculated representative value 622 can be incremented by a fixed amount, the fixed amount being determined by the setting of the tracking speed knob 700. However, if the next acquired data point was still 70 bpm, the next calculated representative value 622 may not change.

The calculated representative value 622 can be incremented or decremented by a fixed default amount, by a percentage (or fraction) of the previous calculated representative value 622, or by an amount that is based on the variance or standard deviation of the acquired data stream 608. For example, if the standard deviation of the acquired data stream 608 is small (i.e., the acquired data stream 608 is relatively stable), the amount by which the calculated representative value 622 is incremented or decremented can also be relatively small. However, if the standard deviation of the acquired data stream 608 is large, the amount by which the calculated representative value 622 is incremented or decremented can also be relatively large to show the variability of the acquired data stream 608.

Figure 10:
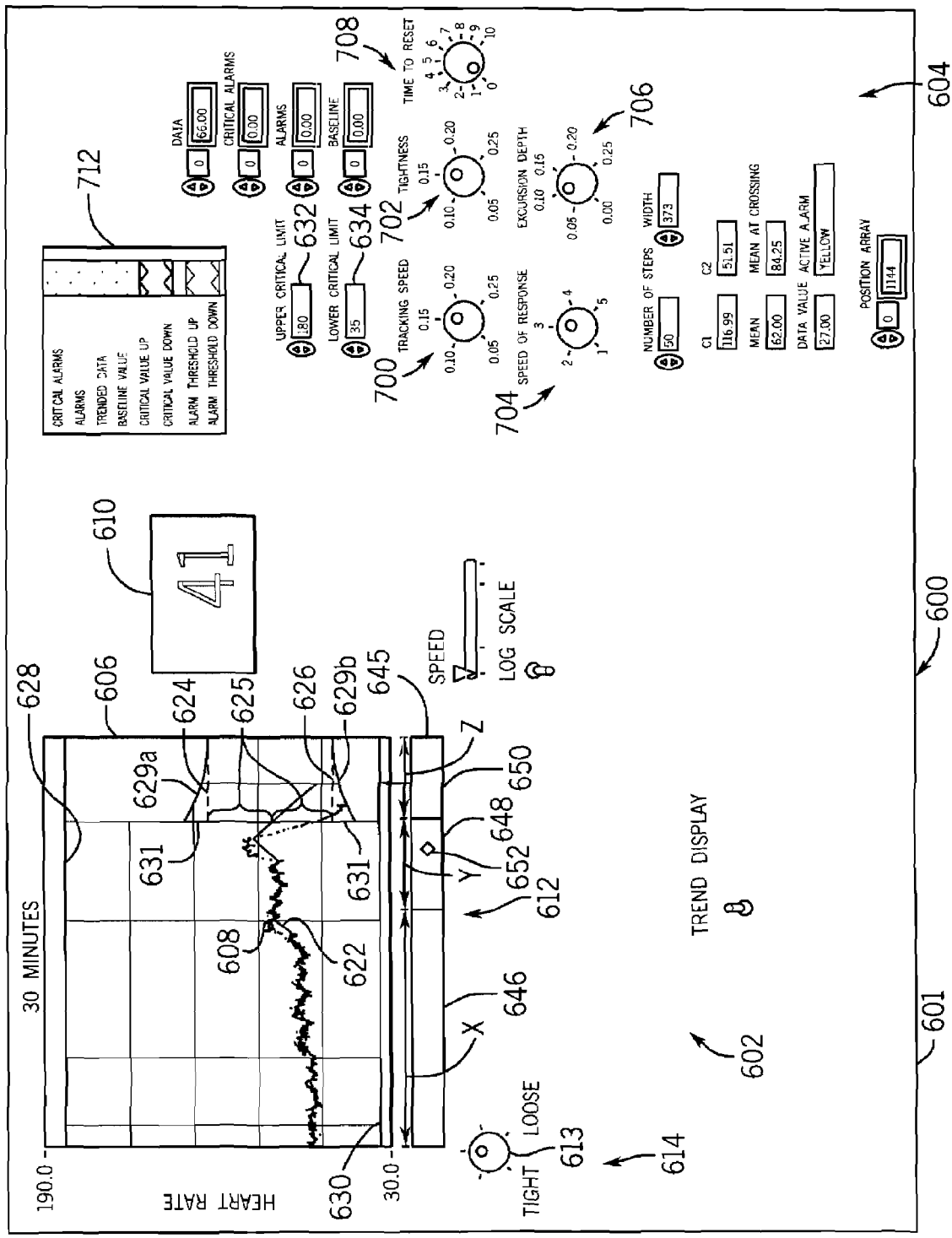
FIG. 10 illustrates the patient monitor and user interface of FIG. 6 with a looser alarm restriction.

The chart 606 can further display an upper alarm threshold 624 (also referred to herein as an upper tracking threshold), a lower alarm threshold 626 (also referred to herein as a lower tracking threshold), an upper extremity limit 628 (also referred to herein as an upper critical limit), a lower extremity limit 630 (also referred to herein as a lower critical limit), an upper alarm limit 629a (as shown in FIG. 10), and a lower alarm limit 629b (as also shown in FIG. 10). The upper and lower alarm limits 629a and 629b are one embodiment of the alarm limit 316 as shown and described with respect to FIG. 2. Specifically, the upper and lower alarm limits 629a and 629b can be defined by the equation AlarmCurve(t)=K+sp$\sqrt{t}$, where "K" is the upper or lower alarm threshold 624 or 626±an excursion value 631, "sp" is a rate of decay, and "t" is time.

The upper and lower tracking thresholds 624 and 626 can be based on the calculated representative value 622, and/or the tracking thresholds 624 and 626 can be constant values that a healthcare provider can manipulate depending on the patient's individual situation. Similarly, the upper and lower extremity limits 628 and 630 can be based on the calculated representative value 622 and/or the extremity limits 628 and 630 can be constant values that can be manipulated by a healthcare provider.

In some embodiments, as illustrated in FIGS. 6-10, the tracking thresholds 624 and 626 can be dependent on the calculated representative value 622, whereas the extremity limits 628 and 630 can be constant values that can be manipulated by a healthcare provider. Specifically, the tracking thresholds 624 and 626 can be controlled by a "tightness" variable (e.g., as represented by a "tightness" knob 702 in FIGS. 6-10). The setting of the tolerance control 614 (as shown in the primary display portion 602) can determine the setting of the tightness variable, which in turn determines how close the tracking thresholds are to the calculated representative value 622. In some embodiments, the tightness variable can be displayed on the user interface 601 in a variety of ways, including without limitation, the tightness knob 702 shown in FIGS. 6-10, a slider with a pointer that slides horizontally or vertically to different settings, a numerical value display, or any other suitable control element.

In some embodiments, the tightness variable can set the tracking thresholds 624 and 626 to be a fixed distance from the calculated representative value 622, and the value of the fixed distance can be determined by the setting of the tightness variable. In other embodiments, the tightness variable can set the tracking thresholds 624 and 626 based on a percentage (or a fraction) of the calculated representative value 622 or the acquired data stream 608. The percentage (or fraction) used to calculate the tracking thresholds 624 and 626 can be dependent on the setting of the tightness variable. In still other embodiments, the tightness variable can set the tracking thresholds 624 and 626 based on a number of standard deviations from the calculated representative value 622 or the acquired data stream 608, and the number of standard deviations used can be determined by the setting of the tightness variable.

Figure 6:
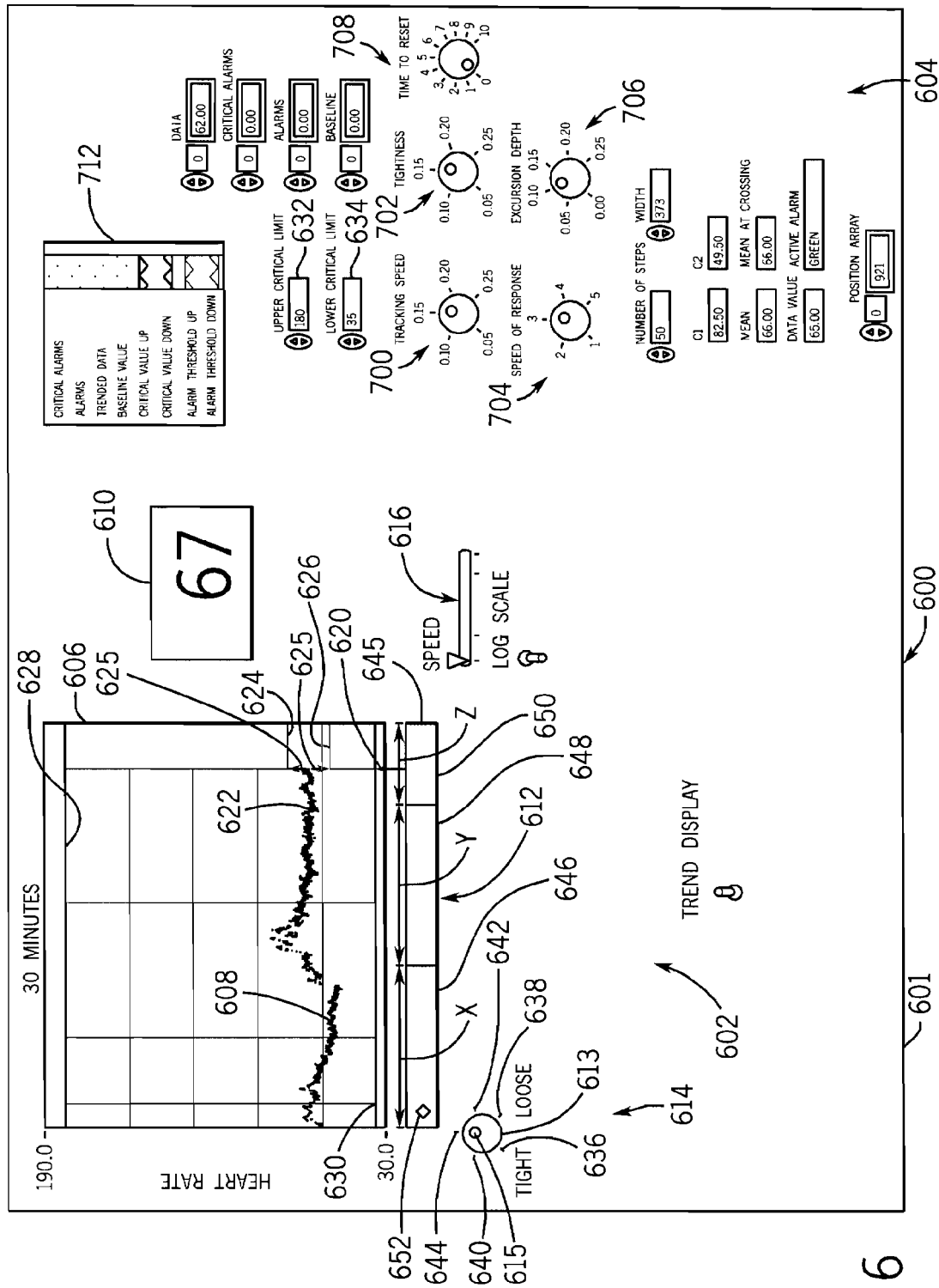
FIG. 6 illustrates a patient monitor and user interface according to one embodiment of the invention.
Figure 7:
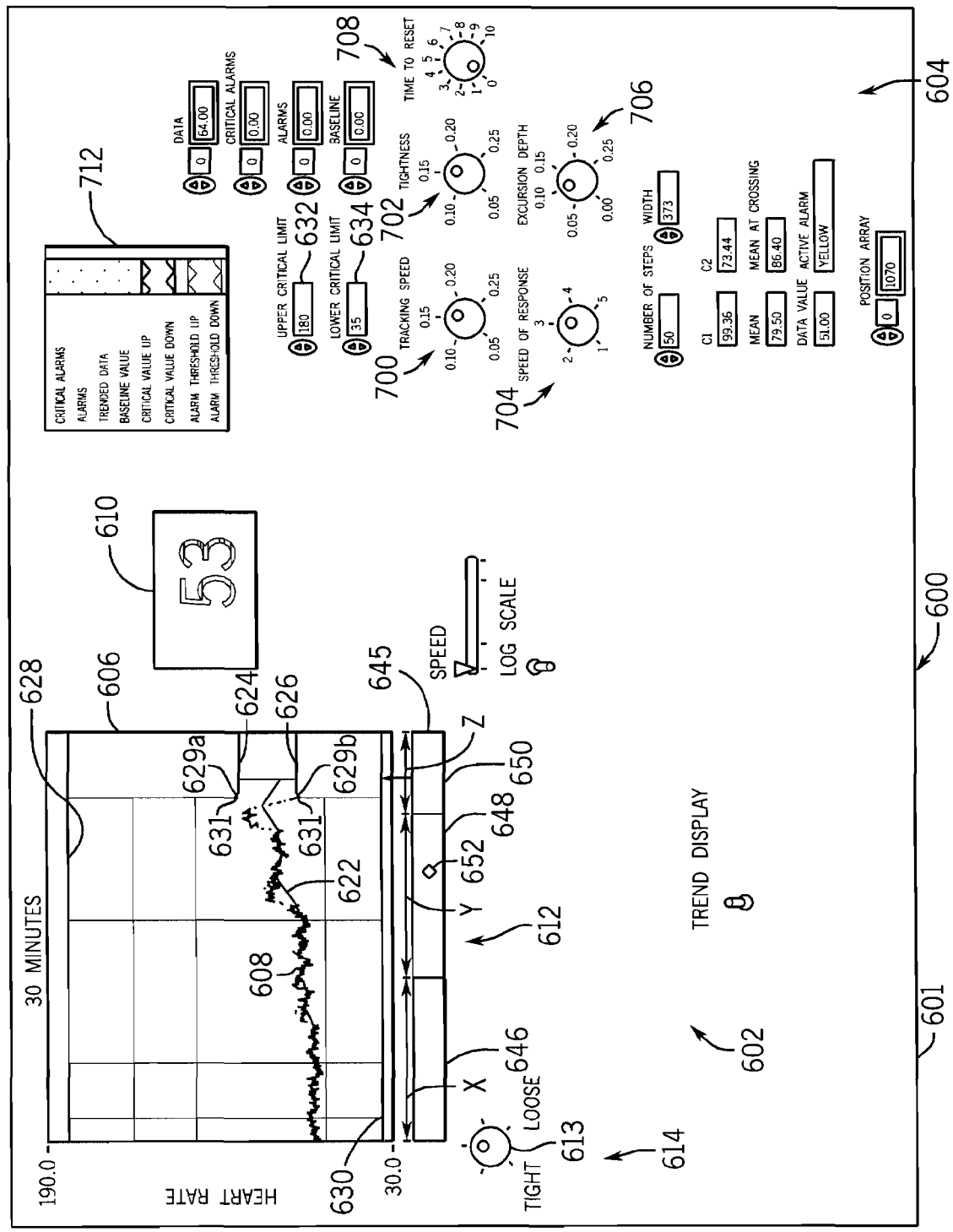
FIG. 7 illustrates the patient monitor and user interface of FIG. 6 during a first alarm condition.

In some embodiments, as shown in FIG. 7, the upper and lower alarm limits 629a and 629b can be at least partially defined by an excursion value 631 (also referred to herein as an "excursion depth") and a decay rate. The decay rate of the upper and lower alarm limits 629a and 629b can be controlled by a "speed of response" variable (e.g., as represented by a "speed of response" knob 704 in FIGS. 6-10). The setting of the tolerance control 614 (as shown in the primary display portion 602) can determine the setting of the speed of response variable, which in turn can determine how quickly the upper and/or lower alarm limit 629a and/or 629b decay. In some embodiments, the speed of response variable can be displayed on the user interface 601 in a variety of ways, including without limitation, the speed of response knob 704 shown in FIGS. 6-10, a slider with a pointer that slides horizontally or vertically to different settings, a numerical value display, or any other suitable control element.

Figure 8:
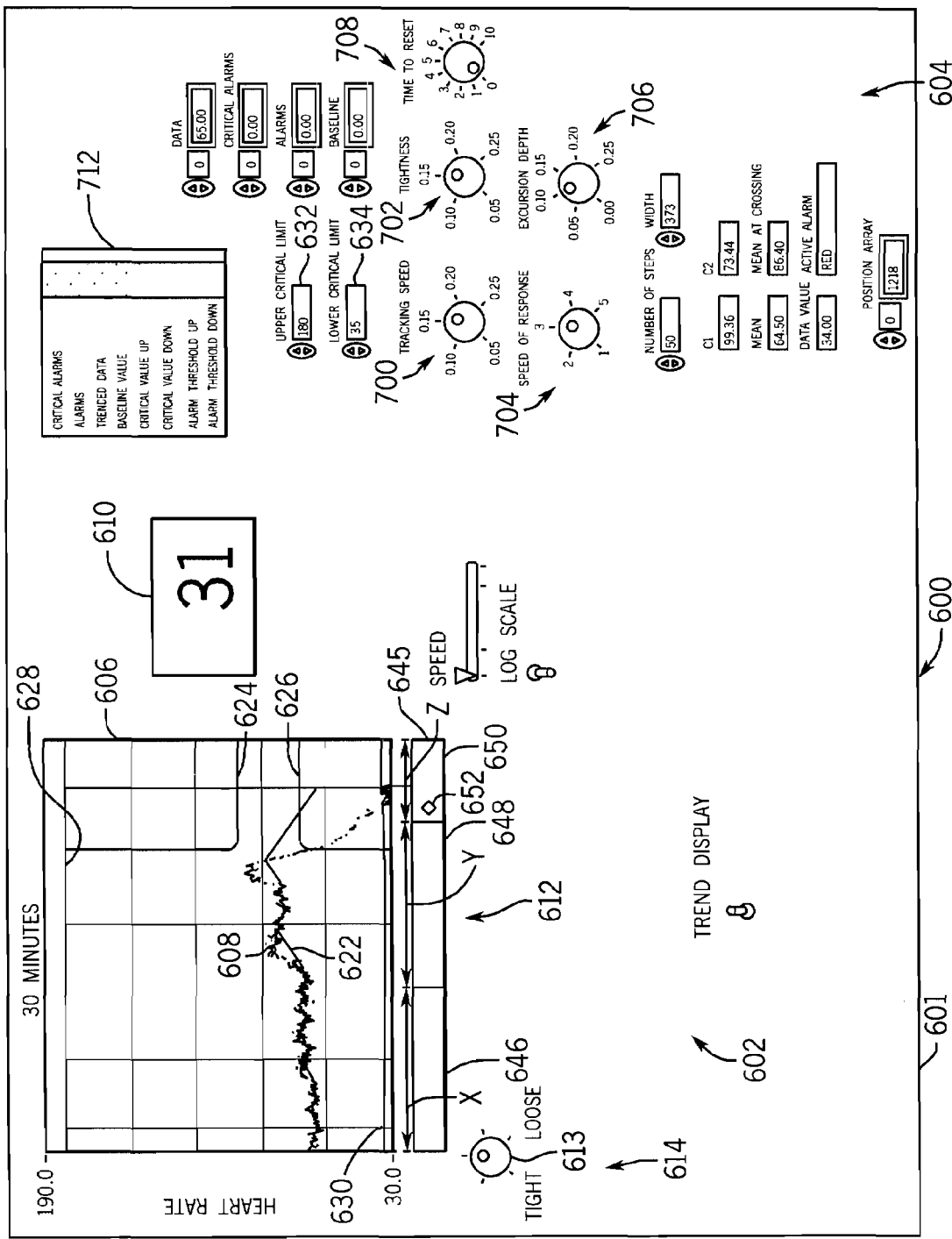
FIG. 8 illustrates the patient monitor and user interface of FIG. 6 during a second alarm condition.
Figure 9:
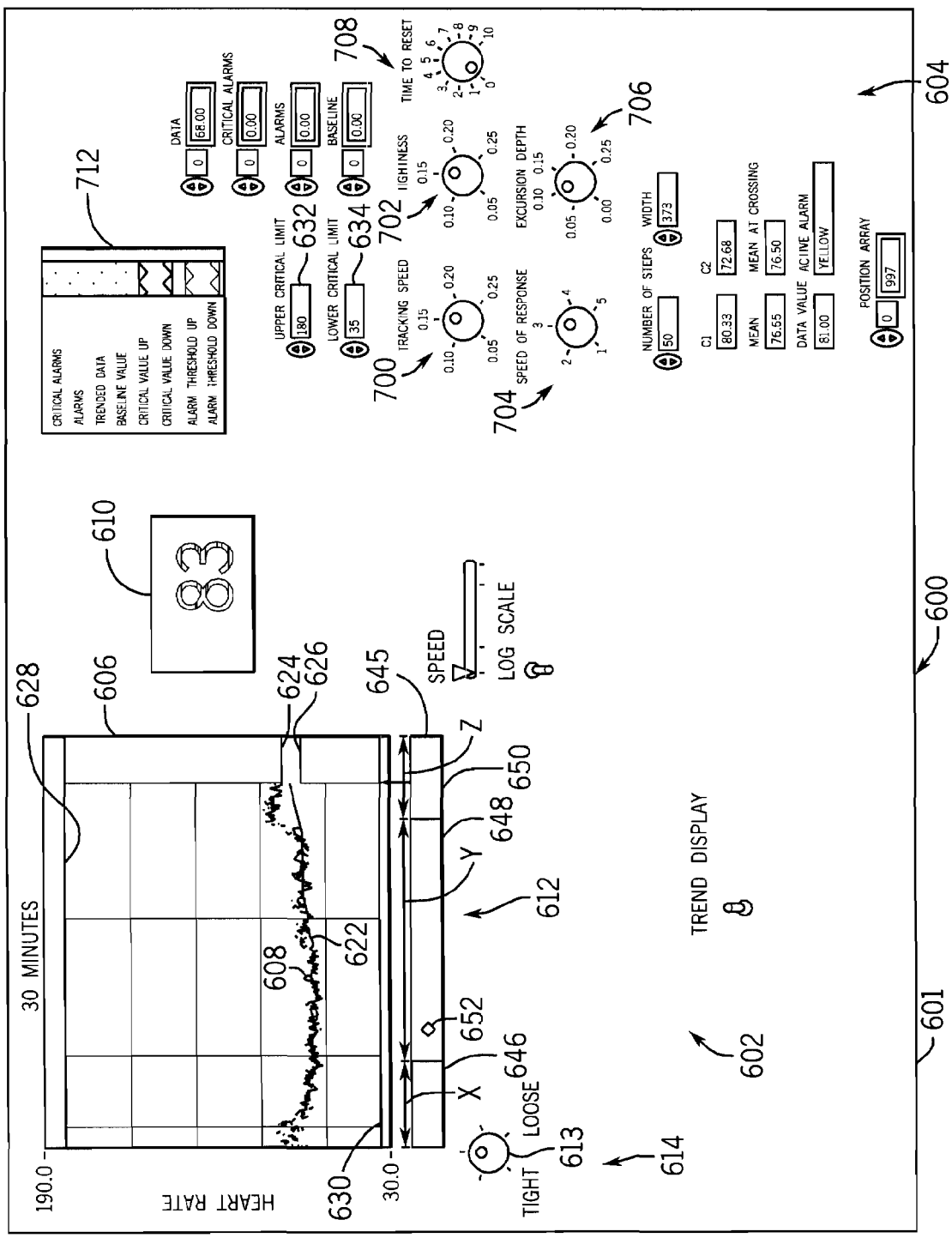
FIG. 9 illustrates the patient monitor and user interface of FIG. 6 with a tighter alarm restriction.

The excursion value 631 of the upper and lower alarm limits 629a and 629b can be controlled by an "excursion depth" variable (e.g., as represented by an "excursion depth" knob 706 in FIGS. 6-10). The setting of the tolerance control 614 (as shown in the primary display portion 602) can determine the setting of the excursion depth variable, which in turn can determine the value of the excursion value 631. As discussed above with respect to FIGS. 2 and 3, the excursion value 631 (or excursion depth) can be the amount the acquired data stream 608 must exceed (above or below) the calculated representative value 622 or the tracking thresholds 624 or 626 in order to trigger the upper or lower alarm limits 629a or 629b (thereby triggering an alarm). In some embodiments, as illustrated in FIGS. 6-10, the excursion value 631 can be the amount the acquired data stream 608 must exceed the upper or lower tracking threshold 624 or 626. Alternatively, the excursion value 631 can be zero, as illustrated in FIG. 9. In some embodiments, the excursion depth variable can be displayed on the user interface 601 in a variety of ways, including without limitation, the excursion depth knob 706 shown in FIGS. 6-10, a slider with a pointer that slides horizontally or vertically to different settings, a numerical value display, or any other suitable control element.

Once the acquired data stream 608 has triggered the upper or lower alarm limit 629a or 629b, the amount of time that must pass before another alarm event can be triggered is controlled by a "time to reset" variable (e.g., as represented by a "time to reset" knob 708 in FIGS. 6-10). The setting of the tolerance control 614 (as shown in the primary display portion 602) can determine the setting of the time to reset variable, which in turn can determine the amount of time that must pass before another alarm event can occur. In some embodiments, the time to reset variable can be displayed on the user interface 601 in a variety of ways, including without limitation, the time to reset knob 708 shown in FIGS. 6-10, a slider, a numerical display, and the like.

The extremity limits 628 and 630 shown in FIGS. 6-10 can be determined by adjusting an upper critical limit value and a lower critical limit value. In some embodiments, such as the embodiment illustrated in FIGS. 6-10, the upper critical limit value can be presented in the user interface 601 in an upper critical limit value display 632, and the lower critical limit value can be presented in the user interface 601 in a lower critical limit value display 634. The upper critical limit value display 632 and the lower critical limit value display 634 can take a variety of forms, including without limitation, a slider with a pointer that slides horizontally or vertically to different settings, a numerical value display (as shown in FIGS. 6-10), a knob, or any other suitable control element. The upper critical limit value display 632 and the lower critical limit value display 634, as shown in the illustrated embodiment, can be adjusted by activating up-arrow or down-arrow buttons or by typing numerical values into the upper and lower critical limit value displays 632 and 634. The upper extremity limit 628 on the chart 606 is linked to the upper critical limit value, and the lower extremity limit 630 on the chart 606 is linked to the lower critical limit value. As the upper and lower critical limit values are changed (e.g., in the upper and lower critical limit value displays 632 and 634), the upper extremity limit 628 and the lower extremity limit 630, respectively, can be changed graphically on the chart 606.

The tolerance control 614 shown in the primary display portion 602 can include a tight/loose knob 613, which can tighten or loosen alarm criteria for a given patient, depending on the patient's individual situation. That is, the tolerance control 614 can control one or more of the upper and lower alarm thresholds 624 and 626, the upper and lower extremity limits 628 and 630, the calculated representative value 622, the alarm communication device 612, and the rate at which any of the criteria can be adjusted.

Referring again to FIG. 6, the tight/loose knob 613 shown in the primary display portion 602 can include a pointer 615. The default position for the pointer 615 can point straight up (i.e., positioned intermediately between an extreme tight setting 636 and an extreme loose setting 638). The tight/loose knob 613 can have discrete settings, such as the extreme tight setting 636, the extreme loose setting 638, an intermediate-tight setting 640, an intermediate-loose setting 642, and an intermediate setting 644 (i.e., the default setting). These settings are illustrated by way of example only, and in other embodiments, the tight/loose knob 613 can be continuously adjustable or can include more or fewer discrete settings. The tight/loose knob 613 can be turned such that the pointer 615 can point to any of the particular settings.

The tight/loose knob 613 can be a hardware knob coupled to the exterior of the patient monitor 600, or the tight/loose knob 613 can be an element of a software program depicted on the user interface 601 (as shown in FIGS. 6-10). If the tight/loose knob 613 is a software element, it can be turned by "clicking and dragging," by "double-clicking" the tight/loose knob 613 to make the pointer 615 shift to a new setting, or by using any other suitable technique for adjusting the setting. In other embodiments of the invention, the tolerance control 614 can include a switch, a slider with a pointer that slides horizontally or vertically to different settings, or any other suitable control element. The control element can be either a hardware element coupled to the exterior of the patient monitor 600 or an element depicted in the software of the user interface 601.

In some embodiments, the tolerance control 614 (e.g., the tight/loose knob 613) can change settings automatically based on the acquired data stream 608 or the calculated representative value 622. For example, the tolerance control 614 can change settings based on one or more of the following: the slope of the acquired data stream 608, the slope of the calculated representative value 622, the stability of the standard deviation of the acquired data stream 608, and the stability of the standard deviation of the calculated representative value 622. In other embodiments, the patient monitor 600 can interface with a network (e.g., as shown in FIG. 1) or a patient data repository, and the tolerance control 614 can be defaulted to a particular setting for a particular patient or tightened or loosened automatically based on various characteristics of a particular patient. In still other embodiments, the tolerance control 614 can change settings automatically based on any of the above factors, but the setting can be manually overridden by a clinician.

The alarm thresholds 624 and 626 can be calculated differently for each of the settings of the tight/loose knob 613. For example, as the pointer 615 of the tight/loose knob 613 moves to a tighter setting (i.e., in a counter-clockwise direction), the tightness variable increases in value (which can be depicted by the tightness knob 702 moving to a tighter setting) and the upper and lower alarm thresholds 624 and 626 each move closer to the calculated representative value 622. As shown by comparing FIG. 6 to FIG. 9, the depth 625 (i.e., the distance between the calculated representative value 622 and each of the alarm thresholds 624 and 626) decreases, such that the distance between the upper alarm threshold 624 and the lower alarm threshold 626 also decreases. Alternatively, as the pointer 615 moves to a looser setting (i.e., in a clockwise direction), the tightness variable decreases in value (which can be depicted by the tightness knob 702 moving to a looser setting), and the upper and lower alarm thresholds 624 and 626 each move further away from the calculated representative value 622. As shown by comparing FIG. 6 to FIG. 10, the depth 625 increases such that the distance between the upper and lower alarm thresholds 624 and 626 increases. In general, increasing the depth 625 and increasing the distance between the upper and lower alarm thresholds 624 and 626 decreases the likelihood that the acquired data stream 608 will cross either the upper alarm threshold 624 or the lower alarm threshold 626.

In some embodiments, manipulating the tight/loose knob 613 can also control and/or alter the alarm communication device 612. In one embodiment, the alarm communication device 612, as shown in the primary display portion 602, can include a one-sided horizontal bar 645 that is divided into the following three regions: a first region 646 having a width x, a second region 648 having a width y and a third region 650 having a width z. The horizontal bar 645 can be a graphical user interface that can describe the current state of a physiological parameter (e.g., heart rate, as shown in FIGS. 6-10) and/or the relative position of the physiological parameter to an alarm condition (e.g., the relative position of one or more of the upper alarm threshold 624, the upper alarm limit 629a, the upper extremity limit 628, the lower alarm threshold 626, the lower alarm limit 629b, and the lower extremity limit 630). The first region 646 of the horizontal bar can represent a region in which the parameter is stable and near the calculated representative value 622. The second region 648 can represent a region in which the parameter has changed significantly. The third region 650 can represent a region in which the parameter has reached a critical value.

An indicator 652 (e.g., a diamond, as shown in FIGS. 6-10) can be displayed on the horizontal bar 645 in order to represent the position of the parameter value with respect to an alarm condition. In some embodiments, as shown in FIGS. 6-10, the indicator 652 can represent the position of the current data point of the acquired data stream 608 relative to an alarm condition. In other embodiments, the indicator 652 can represent the position of the calculated representative value 622 relative to an alarm condition.

As shown in FIG. 6, the current data point (as marked on the chart 606 by the pointer 620 and displayed in the current data display 610) of the acquired data stream 608 may be within the region on the chart 606 between the upper and lower alarm thresholds 624 and 626. More particularly, the current data point may be positioned between the calculated representative value 622 and either of the upper or lower alarm threshold 624 or 626 plus the excursion value 631 (if the excursion value is greater than zero). In this situation, the indicator 652 can be positioned in the first region 646 of the horizontal bar 645. The width x of the first region 646 can be proportional to the depth 625, or proportional to the depth 625 plus the excursion value 631 (if the excursion value 631 is greater than zero, as controlled by the excursion depth knob 706).

In some embodiments, as shown in FIGS. 6-10, the upper alarm threshold 624 and the lower alarm threshold 626 can be positioned symmetrically on opposite sides of the calculated representative value 622, so that the depth 625 to the upper alarm threshold 624 is equal to the depth 625 to the lower alarm threshold 626. However, in other embodiments of the invention, the depth 625 to the upper alarm threshold 624 can be different from the depth 625 to the lower alarm threshold 626. In some embodiments, the width x of the first region 646 can be proportional to the distance between the upper alarm threshold 624 and the lower alarm threshold 626. One or more of the indicator 652, the acquired data stream 608, the calculated representative value 622, the current data display 610, and the first region 646 can be colored, can be patterned, or can have other suitable identifying characteristics in order to indicate that the parameter is stable and/or near the calculated representative value 622. For example, the color green can represent a stable parameter associated with the first region 646.

As shown in FIG. 7, the current data point of the acquired data stream 608 may be within a region on the chart 606 between the upper alarm limit 629a (or the upper alarm threshold 624, if the excursion value is zero) and the upper extremity limit 628. Also, the current data point may be within a region on the chart 606 between the lower alarm limit 629b (or the lower alarm threshold 626, if the excursion value 631 is zero) and the lower extremity limit 630. In either of these situations, the indicator 652 can move into the second region 648 of the horizontal bar 645. The bounds of the second region 648 can represent the upper alarm limit 629a and the upper extremity limit 628, the upper alarm threshold 624 and the upper extremity limit 628, the lower alarm limit 629a and the lower extremity limit 630, or the lower alarm threshold 624 and the lower extremity limit 630. The width y of the second region 648 can be proportional to the distance between the upper alarm limit 629a (or the upper alarm threshold 624) and the upper extremity limit 628 when the acquired data stream 608 is greater than the calculated representative value 622. Also, the width y of the second region 648 can be proportional to the distance between the lower alarm limit 629b (or the lower alarm threshold 626) and the lower extremity limit 630 when the acquired data stream 608 is less than the calculated representative value 622. The width y of the second region 648 can depend on whether the acquired data stream 608 is above or below the calculated representative value 622. One or more of the indicator 652, the acquired data stream 608, the calculated representative value 622, the current data display 610, and the second region 648 can be colored, can be patterned, or can have other suitable identifying characteristics in order to indicate that the parameter may have changed significantly, or may be moving further away from the calculated representative value 622. For example, the color yellow can represent a parameter associated with the second region 648.

As shown in FIG. 8, the current data point of the acquired data stream 608 may be above the upper extremity limit 628 or below the lower extremity limit 630. In this situation, the indicator 652 can move into the third region 650 of the horizontal bar 645 in order to indicate that the acquired data stream 608 has reached a critical value. One or more of the indicator 652, the acquired data stream 608, the calculated representative value 622, the current data display 610, and the third region 650 can be colored, can be patterned, or can have other suitable identifying characteristics in order to indicate that the parameter may have reached a critical value. For example, the color red can represent a parameter associated with the third region 650.

In some embodiments, the bounds of the third region 650 do not move based on the setting of the tight/loose knob 613. This is because the far right limit of the third region 650 does not actually have a limit, because the acquired data stream 608 can go as high or as low as physiologically possible (i.e., the acquired data stream does not have an exact upper or lower limit). For example, the patient's heart rate can go as high as physiologically possible or as low as zero, both of which are "critical values." As a result, the width z of the third region 650 can be set to a default size. When the current data point of the acquired data stream 608 crosses either the upper extremity limit 628 or the lower extremity limit 630, the indicator 652 can move into the third region 650 to indicate that the current data point has reached a critical value. In other embodiments of the invention, the lower limit of the third region 650 can move when either the upper extremity limit 628 or the lower extremity limit 630 is changed.

The upper and lower alarm thresholds 624 and 626, which can be controlled by the tight/loose knob 613, can determine the bounds and the widths x, y and z of the first region 646, the second region 648, and the third region 650, respectively. As a result, when the upper and lower alarm thresholds 624 and 626 are changed, the bounds and the widths x, y and z of the regions 646, 648 and 650 can change, and the horizontal bar 645 can be updated to reflect that change.

In some embodiments, the horizontal bar 645 may not be associated with specific numeric values in order to visually represent the relationship between the current data point and any alarm condition. The alarm condition can be associated with one or more of the upper alarm threshold 624, the upper alarm limit 629a, the upper extremity limit 628, the lower alarm threshold 626, the lower alarm limit 629b, and the lower extremity limit 630. This configuration can allow a healthcare provider to visually perceive when a patient is moving away from a "normal" or stable condition (e.g., away from the calculated representative value 622) or moving away from an alarm condition. In some embodiments, the horizontal, one-sided configuration of the alarm communication device 612 shown in FIGS. 6-10 can minimize any misconception that a middle region is normal and edge regions are abnormal (which may be the case with vertically-oriented and/or two-sided devices). However, in some embodiments of the invention, the alarm communication device 612 can be of any shape (i.e., a shape other than an elongated bar), can have a two-sided configuration, and/or can be oriented vertically.

In some embodiments, as shown in FIGS. 6-8, the acquired data stream 608 may cross either the upper tracking threshold 624 (or the upper alarm limit 629a, if the excursion value 631 is greater than zero) or the lower tracking threshold 626 (or the lower alarm limit 629b, if the excursion value 631 is greater than zero). In either of these situations, both the upper tracking threshold 624 and the lower tracking threshold 626 can remain fixed until the acquired data stream 608 returns to the region on the chart 606 between the upper alarm limit 629a (or the upper alarm threshold 624) and the lower alarm limit 629b (or lower tracking threshold 626). In other words, the upper and lower tracking thresholds 624 and 626 can remain fixed until the indicator 652 returns to the first region 646 of the horizontal bar 645.

Whether the tolerance control 614 (e.g., the tight/loose knob 613 or another type of tolerance control) is manipulated manually or automatically, the "tightness" and the "depth" of the various alarm thresholds or limits (e.g., one or more of the upper alarm threshold 624, the upper alarm limit 629a, the upper extremity limit 628, the lower alarm threshold 626, the lower alarm limit 629b, and the lower extremity limit 630) can be set on an individual basis for each patient. For example, a first patient may require an alarm at a heart rate of 50 bpm, while a second patient may be stable at this heart rate. Accordingly, the first patient may require a tighter setting on the tolerance control 614 than the second patient.

In addition to controlling the "tightness" and "depth" variables of the alarm thresholds 624 and 626, the tight/loose knob 613 can also control "tracking speed" and "speed of response" variables. As shown in FIGS. 6-10, these variables can be represented by various knobs in the secondary display portion 604 of the user interface 601. In addition, the tracking speed knob 700, the tightness knob 702, the speed of response knob 704, and the excursion depth knob 706 can be controlled by the tight/loose knob 613.

As mentioned above, the secondary display portion 604 of the user interface 601 can include the tracking speed knob 700, the tightness knob 702, the speed of response knob 704, the excursion depth knob 706, and the time to reset knob 708. In some embodiments, the tracking speed knob 700, the tightness knob 702, the speed of response knob 704, the excursion depth knob 706, and the time to reset knob 708 can each include discrete settings that can correspond to the discrete settings of the tight/loose knob 613. For example, as illustrated in FIG. 6, when the pointer 615 of the tight/loose knob 613 is pointing to the intermediate setting 644 (i.e., straight up), the tracking speed knob 700, the tightness knob 702, and the speed of response knob 704 can all also be pointing straight up to an intermediate setting. The excursion depth knob 706 can be pointing to a setting marked "0.10" just left of the straight-up position. Thus, in some embodiments, each setting on the tight/loose knob 613 can correspond to a discrete setting on each of the knobs 700, 702, 704, 706 and 708. In other embodiments, the knobs 700, 702, 704, 706 and 708 can be independently controlled, either manually or automatically based on patient data, to override the setting dictated by the tight/loose knob 613. In embodiments in which the knobs 700, 702, 704, 706 and 708 are not used, the tracking speed variable, the tightness variable, the speed of response variable, the excursion depth variable, and the time to reset variable can be independently controlled, either manually or automatically based on patient data, to override the setting dictated by the tight/loose knob 613. Embodiments that allow for these variables and/or the knobs 700, 702, 704, 706 and 708 to be independently controlled can allow for more precise fine-tuning of alarm thresholds to meet specific patient situations. The discrete values shown in FIGS. 6-10 are shown by way of example only, and other suitable discrete or continuous values can be used.

The secondary display portion 604 can further include a legend 712 for the chart 606, which can include colors, patterns, or other features for identifying one or more of the following: the upper extremity limit 628 (also referred to as the "Critical Value Up"), the lower extremity limit 630 (also referred to as the "Critical Value Dwn"), the upper alarm threshold 624 (also referred to as the "Alarm Threshold Up"), the lower alarm threshold 626 (also referred to as the "Alarm Threshold Dwn"), the acquired data stream 608 when it is stable (also referred to as "Trended Data"), the acquired data stream 608 when it has crossed an alarm threshold 624 or 626 (also referred to as "Alarms"), the acquired data stream 608 when it has crossed an extremity limit 628 or 630 (also referred to as "Critical Alarms"), and the calculated representative value 622 (also referred to as "Baseline Value").

In some embodiments, the identifiers for the tracking thresholds 624 and 626, the alarm limits 629a and 629b, and the upper and lower extremity limits 628 and 630 can be shown on the chart 606 only temporarily after the tight/loose knob 613 is clicked, activated, or otherwise adjusted. Such embodiments can help prevent the chart 606 from becoming too cluttered or cumbersome. In such embodiments, a user can see how adjusting the tight/loose knob 613 affects the various alarm thresholds and limits, but the identifiers fade away or disappear from the chart 606 after a predetermined amount of time (e.g., 2-3 seconds after adjusting the tight/loose knob 613). In other embodiments, the identifiers for the various alarm thresholds and limits can be continuously displayed on the chart 606 throughout a patient monitoring process.

Various features and advantages of the invention are set forth in the following claims.

The invention claimed is:

1. A graphical user interface for displaying an alarm condition on a patient monitor, the graphical user interface comprising:
 a chart that displays a physiological parameter of a patient;
 an alarm communication device separate from the chart that indicates a state of the physiological parameter displayed by the chart, the alarm communication device including at least a stable region, an intermediate region, and a critical region, at least one of the intermediate region and the critical region representing the alarm condition; and
 a tolerance control that adjusts at least one of a boundary and a width of at least one of the stable region, the intermediate region, and the critical region in order to adjust the alarm condition.

2. The graphical user interface of claim 1 wherein the alarm communication device includes a horizontal bar divided into at least the stable region, the intermediate region, and the critical region.

3. The graphical user interface of claim 1 wherein the alarm communication device includes an indicator representing a current data point.

4. The graphical user interface of claim 1 wherein the alarm communication device includes an indicator representing a calculated representative value for the physiological parameter.

5. The graphical user interface of claim 1 wherein an upper boundary of the stable region corresponds to at least one of an upper tracking threshold, an upper alarm limit, a lower tracking threshold, and a lower alarm limit.

6. The graphical user interface of claim 1 wherein an upper boundary of the intermediate region corresponds to at least one of an upper extremity limit and a lower extremity limit.

7. The graphical user interface of claim 1 wherein the width of the stable region is proportional to a depth between a calculated representative value and at least one of an upper tracking threshold and a lower tracking threshold.

8. The graphical user interface of claim 7 wherein the width of the stable region is proportional to the depth plus an excursion value.

9. The graphical user interface of claim 1 wherein each one of the stable region, the intermediate region, and the critical region is displayed in a different color.

10. The graphical user interface of claim 1 wherein
 the alarm communication device includes an indicator representing a current data point, and
 the indicator has a color, the color of the indicator being at least partially dependent upon the position of the indicator with respect to at least one of the stable region, the intermediate region, and the critical region.

11. The graphical user interface of claim 1 wherein at least one of a boundary and the width of the critical region is a default setting that cannot be adjusted with the tolerance control.

12. The graphical user interface of claim 1 wherein the tolerance control can adjust an upper tracking threshold and a lower tracking threshold in order to determine at least one of the boundary and the width of at least one of the stable region and the intermediate region.

13. The graphical user interface of claim 1 wherein the alarm communication device is an elongated device oriented vertically or horizontally.

14. The graphical user interface of claim 1 wherein the tolerance control can adjust at least one of the boundary and the width of at least one of the stable region and the intermediate region for a particular patient.

15. The graphical user interface of claim 1 wherein the tolerance control can adjust at least one of tracking speed, tightness, speed of response, excursion depth, and time to reset.

16. The graphical user interface of claim 1 and further comprising at least one of a tracking speed knob, a tightness knob, a speed of response knob, an excursion depth knob, and a time to reset knob, each knob being controlled individually for a particular patient.

17. A graphical user interface for displaying an alarm condition on a patient monitor, the graphical user interface comprising:
    a chart including:
        an acquired data stream of a physiological parameter;
        an upper tracking threshold displayed above the acquired data stream; and
        a lower tracking threshold displayed below the acquired data stream;
    an alarm communication device separate from the chart that indicates a state of the physiological parameter displayed by the chart, the alarm communication device including at least a stable region, an intermediate region, and a critical region, at least one of the intermediate region and the critical region representing the alarm condition; and
    a tolerance control that adjusts at least one of the upper tracking threshold and the lower tracking threshold in order to adjust the alarm condition.

18. The graphical user interface of claim 17, wherein the acquired data stream has a color, the color of the acquired data stream being at least partially dependent upon the alarm condition.

19. The graphical user interface of claim 17 wherein the tolerance control adjusts at least one of the upper tracking threshold and the lower tracking threshold based on a calculated representative value.

20. The graphical user interface of claim 19 wherein the calculated representative value can be incremented when the acquired data stream is greater than a previous calculated representative value and can be decremented when the acquired data stream is less than the previous calculated representative value.

21. The graphical user interface of claim 20 wherein the calculated representative value is incremented or decremented by at least one of a fixed default amount, a percentage of the previous calculated representative value, and an amount based on a standard of deviation of the acquired data stream.

22. The graphical user interface of claim 17 wherein at least one of the upper tracking threshold and the lower tracking threshold are constant values that can only be adjusted by a healthcare provider.

23. The graphical user interface of claim 17 wherein the tolerance control adjusts at least one of the upper tracking threshold and the lower tracking threshold based on a standard deviation of at least one of a calculated representative value and the acquired data stream.

24. The graphical user interface of claim 17 wherein the chart includes at least one of an upper alarm limit and a lower alarm limit, the upper alarm limit being based on the upper tracking threshold and an excursion value, the lower alarm limit being based on the lower tracking threshold and the excursion value.

25. The graphical user interface of claim 24 wherein the excursion value represents an amount by which the acquired data stream must exceed one of the upper tracking threshold and the lower tracking threshold for the alarm condition.

26. The graphical user interface of claim 17 and further comprising an alarm communication device that indicates a state of the physiological parameter, the alarm communication device including a stable region, an intermediate region, and a critical region, the critical region representing the alarm condition.

27. The graphical user interface of claim 17 wherein the chart includes at least one of an upper extremity limit displayed above the upper tracking threshold and a lower extremity limit displayed below the lower tracking threshold.

28. The graphical user interface of claim 17 and further comprising a pointer that indicates a data point on the chart corresponding to currently-acquired data.

29. The graphical user interface of claim 28 and further comprising a current data display including a numeric value representing the data point corresponding to the currently-acquired data.

30. The graphical user interface of claim 29 wherein the current data display has a color, the color of the current data display being at least partially dependent upon the alarm condition.

31. The graphical user interface of claim 17 wherein the acquired data stream includes heart rate data.

32. The graphical user interface of claim 17 wherein the tolerance control adjusts at least one of the upper tracking threshold and the lower tracking threshold automatically based on at least one of the acquired data stream and a calculated representative value.

33. The graphical user interface of claim 32 wherein the tolerance control adjusts at least one of the upper tracking threshold and the lower tracking threshold automatically based on at least one of a slope and a standard deviation of at least one of the acquired data stream and the calculated representative value.

34. The graphical user interface of claim 17 wherein the tolerance control adjusts one of the upper tracking threshold and the lower tracking threshold automatically based on characteristics of a particular patient.

35. A method of displaying an alarm condition with respect to a physiological parameter being acquired form a patient, the method comprising:
    indicating whether a physiological parameter is within one of a stable region, an intermediate region, and a critical region, on an alarm communication device that is separate from a chart displaying the physiological parameter, at least one of the intermediate region and the critical region representing the alarm condition; and
    adjusting at least one of a boundary and a width of at least one of the stable region, the intermediate region, and the critical region in order to adjust the alarm condition.

36. The method of claim 35 and further comprising displaying an indicator representing a position of a current data point.

37. The method of claim 35 and further comprising displaying an indicator representing a calculated representative value for the physiological parameter.

38. The method of claim 35 and further comprising adjusting a width of the intermediate region in proportion to a depth between a calculated representative value and at least one of an upper tracking threshold and a lower tracking threshold.

39. The method of claim 38 wherein the adjusting the width of the intermediate region include adjusting the width of the intermediate region in proportion to the depth plus an excursion value.

40. The method of claim 35 and further comprising displaying each one of the stable region, the intermediate region, and the critical region in a different color.

41. The method of claim 35 and further comprising adjusting an upper alarm threshold and a lower tracking threshold in order to determine at least one of the boundary and the width of at least one of the stable region and the intermediate region.

42. The method of claim 35 and further comprising adjusting at least one of the boundary and the width of at least one of the stable region and the intermediate region for a particular patient.

43. A method of displaying an alarm condition with respect to a physiological parameter being acquired from a patient, the method comprising;
    displaying a chart including:
        an acquired data stream of the physiological parameter;
        an upper tracking threshold displayed above the acquired data stream; and
        a lower tracking threshold displayed below the acquired data stream;
    displaying an alarm communication device separate from the chart that indicates a state of the physiological parameter displayed by the chart, the alarm communication device including at least a stable region, an intermediate region, and a critical region, at least one of the intermediate region and the critical region representing the alarm condition; and
    adjusting at least one of the upper tracking threshold and the lower tracking threshold in order to adjust the alarm condition.

44. The method of claim 43 and further comprising adjusting at least one of the upper tracking threshold and the lower tracking threshold based on a calculated representative value.

45. The method of claim 44 and further comprising incrementing the calculated representative value when the acquired data stream is greater than a previous calculated representative value and decrementing the calculated representative value when the acquired data stream is less than the previous calculated representative value.

46. The method of claim 44 and further comprising incrementing or decrementing the calculated representative value by at least one of a fixed default amount, a percentage of the previous calculated representative value, and an amount based on a standard of deviation of the acquired data stream.

47. The method of claim 43 and further comprising adjusting at least one of the upper tracking threshold and the lower tracking threshold based on a standard deviation of at least one of a calculated representative value and the acquired data stream.

48. The method of claim 43 and further comprising displaying a chart including at least one of an upper alarm limit and a lower alarm limit, the upper alarm limit being based on the upper tracking threshold and an excursion value, the lower alarm limit being based on the lower tracking threshold and the excursion value.

49. The method of claim 43 and further comprising displaying at least one of an upper extremity limit above the upper tracking threshold and a lower extremity limit below the lower tracking threshold.

50. The method of claim 43 and further comprising indicating a data point on the chart corresponding to currently-acquired data.

51. The method of claim 50 and further comprising displaying a numeric value representing the data point corresponding to the currently-acquired data.

52. The method of claim 43 and further comprising displaying an acquired data stream including heart rate data.

53. The method of claim 43 and further comprising adjusting at least one of the upper tracking threshold and the lower tracking threshold automatically based on at least one of the acquired data stream and a calculated representative value.

54. The method of claim 53 and further comprising adjusting at least one of the upper tracking threshold and the lower tracking threshold automatically based on at least one of a slope and a standard deviation of at least one of the acquired data stream and the calculated representative value.

55. The method of claim 43 and further comprising adjusting one of the upper tracking threshold and the lower tracking threshold automatically based on characteristics of a particular patient.

56. A device for displaying an alarm condition with respect to a physiological parameter being acquired from a patient, the device comprising:
    means for indicating a state of a physiological parameter separate from a means for displaying the physiological parameter, the state being within one of a stable region, an intermediate region, and a critical region, at least one of the intermediate region and the critical region representing the alarm condition; and
    means for adjusting at least one of a boundary and a width of at least one of the stable region, the intermediate region, and the critical region in order to adjust the alarm condition.

* * * * *

UNITED STATES PATENT AND TRADEMARK OFFICE
CERTIFICATE OF CORRECTION

PATENT NO. : 7,639,145 B2 Page 1 of 1
APPLICATION NO. : 10/834625
DATED : December 29, 2009
INVENTOR(S) : Lawson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1644 days.

Signed and Sealed this

Ninth Day of November, 2010

David J. Kappos
*Director of the United States Patent and Trademark Office*